United States Patent [19]

Bernard et al.

[11] Patent Number: 4,493,901

[45] Date of Patent: Jan. 15, 1985

[54] REGENERATION PROCESS OF AN AROMATIZATION CATALYST CONTAINING A GROUP VIII METAL ON A ZEOLITE

[75] Inventors: Jean R. Bernard, Solaize; Michèle Breysse, Caluire, both of France

[73] Assignee: Elf France, Paris, France

[21] Appl. No.: 414,675

[22] Filed: Sep. 3, 1982

[30] Foreign Application Priority Data

Sep. 9, 1981 [FR] France .................................. 81 17064

[51] Int. Cl.³ .......................... B01J 23/96; B01J 29/38; C07C 5/393; C10G 35/085
[52] U.S. Cl. ....................................... 502/37; 208/140; 585/419
[58] Field of Search ......................... 252/415; 208/140; 585/419; 502/37

[56] References Cited

U.S. PATENT DOCUMENTS

| | | | |
|---|---|---|---|
| 3,637,524 | 1/1972 | Johnson et al. | 252/415 |
| 3,835,063 | 9/1974 | Davis, Jr. et al. | 252/415 |
| 4,104,320 | 8/1978 | Bernard et al. | 585/419 |

FOREIGN PATENT DOCUMENTS 2325289  4/1977  France ................................ 252/415

Primary Examiner—P. E. Konopka
Attorney, Agent, or Firm—Birch, Stewart, Kolasch & Birch

[57] ABSTRACT

The invention relates to a process for the regeneration of an aromatization catalyst containing a metal of Group VIII supported on zeolite, the process being such that the catalyst is subjected to combustion, and then to oxychloration.

According to the invention, the oxychloration step is followed by a hydratation step.

The treatment according to the invention increases the selectivity of the regenerated catalyst.

6 Claims, No Drawings

REGENERATION PROCESS OF AN AROMATIZATION CATALYST CONTAINING A GROUP VIII METAL ON A ZEOLITE

DEFINITION OF THE GENERAL FIELD OF THE INVENTION

The present invention relates to a regeneration process of a catalyst for the aromatization or dehydrocyclization of paraffinic hydrocarbons. More particularly, it concerns the regeneration of catalysts containing at least one metal from Group VIII of the Periodic Table of the Elements supported in a zeolite, especially a zeolite-L.

BACKGROUND OF THE INVENTION

For many years it has been known to aromatize a feed that is, above all, paraffinic, in the presence of platinum/chlorinated alumina type catalysts. More recently, this aromatization has been realized in the presence of catalysts containing a metal of Group VIII of the Periodic Table of the Elements supported on a zeolite, especially a zeolite-L, exchanged, preferably, at more than 90% by alkaline ions.

U.S. Pat. No. 4,104,320 in the name of the applicant describes such a catalyst. These catalysts have the advantage of being easily reactivable through hydrogen treatment.

French patent publication No. 2,484,401 in the name of the applicant describes a process for the dehydrocyclization of paraffins using two reactions, one of the reactors producing aromatic hydrocarbons, while the other is swept by hydrogen produced in the first reactor in order to reactivate the catalyst; thereafter, the reactors are commuted. Such a process allows lengthy operating without loss of selectivity of the catalyst. Nevertheless, after a considerable time clogging of the catalyst due to coke deposit occurs and the catalyst can no longer satisfy its role and must therefore be regenerated.

It is known to regenerate aromatization catalysts by burning coke in an atmosphere containing oxygen. This combustion is often preceded by a sweeping step with hydrogen or nitrogen. The catalyst is thereafter subjected to oxychlorination by heat treatment by mixtures of air and chlorine or, further, by chlorinated compounds such as $CCl_4$ in the presence of air.

When this regeneration process is applied to the catalyst of the type formed of metal of Group VIII supported on zeolite, a large part of its selectivity is effectively restored. Nevertheless, it has never been possible to obtain exactly the values of the initial selectivity.

SUMMARY DEFINITION OF THE INVENTION

The applicant has now found, and this is the object of the present invention, that it is possible to improve the selectivity of the catalysts thus treated and to obtain values close to, if not equal to, the initial values, by following an oxychloration step with a hydratation step.

According to an embodiment of the invention, this hydratation takes place during cooling of the catalyst after the oxychlorination step by adding to the cooling air a quantity of water in the range of 10% by weight with respect to the catalyst at a temperature not exceeding 200° C.

Other aims and advantages of the present invention will appear by reading through the following examples, being supplied by way of nonlimitative illustration.

DETAILED DESCRIPTION OF ONE EMBODIMENT OF THE INVENTION

The catalyst used in these examples, of the type described in U.S. Pat. No. 4,104,320, is obtained by dry impregnating pellets of a zeolite by dinitro-diaminoplatinum $Pt(NH_3)_2(NO_2)_2$. Then the pellets are treated by KCl at boiling temperature, are washed by a KOH solution at pH10 until elimination of the $Cl^-$ ions, and thereafter are dried and calcined for 3 hours at 400° C.

EXAMPLE 1

This catalyst is placed in a catalytic reforming reactor and is treated by hydrogen at temperatures ranging up to 500° C., the temperature being allowed to drop to 460° C.; the activity and selectivity of the catalyst are measured by introducing n-hexane under the following conditions:
atmospheric pressure
$H_2$/hydrocarbon ratio: 18
contact time 0.85 s
460° C.

The results are compiled hereinafter in Table I under the indication "Catalyst 1".

The catalyst is used during several months for dehydrocyclization reactions under the conditions described in French patent application No. 80 10 411, published as Publication No. 2,484,401, until its activity and its selectivity become insufficient. At this moment, the catalyst is analyzed and it is observed that it contains 5.1% carbon. Measured under the same conditions as those of the new catalyst, its activity and its selectivity are listed in Table 1 under the reference "Catalyst 2".

This catalyst is subject to a treatment by hydrogen for 12 hours at 460° C.; it is left to cool to 385° C. after sweeping with nitrogen (for 30 minutes), then at this temperature, sweeping air of the reactor is fed: the temperature rises suddenly to 412° C. and then stabilizes at 395° C. Calcination occurs for 5 hours at 510° C. in the presence of air. Then $CCl_4$ in three fractions is introduced into the air stream, as known per se, the quantities of $CCl_4$ in said air stream being such that the percentage of chlorine with respect to the weight of the catalyst is of about 1%. The catalyst is left for 5 hours at 510° C., then it is activated by hydrogen as known per se. Thus, a regenerated catalyst is obtained according to the prior art; it is called "Catalyst 3" in Table 1.

EXAMPLE 2

Operating occurs as in Example 1; however, during air cooling of the catalyst, after oxychlorination and prior to activation by hydrogen, a quantity of water equal to 10% by weight with respect to the catalyst is introduced at a temperature of 200° C. Thus, "Catalyst 4", as shown in Table I, is obtained.

EXAMPLE 3

Operating occurs as in Example 2, but water is introduced at 60° C. Thus, "Catalyst 5", as shown in Table 1, is obtained.

EXAMPLE 4

Operating occurs as previously described, but the used catalyst is ground prior to calcination. After oxychlorination, 10% of the stream containing water at ambient temperature is added. Thus "Catalyst 6", as shown in Table 1, is obtained.

All of the catalysts 1 to 6 are subjected to tests in a dynamic micro-reactor, the dehydrocyclization test is accomplished in the presence of n-hexane at 460° C., with a contact time of 0.85 seconds, and $H_2$/hydrocarbon ratio=18 after reduction of the catalyst by hydrogen.

TABLE I

| CATALYST NUMBER | N-HEXANE CONVERSION | Lightweight Effluents % | S* | $IC_6$ Isohexanes % | S | *MCP % | S | BENZENE % | S |
|---|---|---|---|---|---|---|---|---|---|
| 1 | 84 | 3.3 | 3.9 | 3.4 | 4.0 | 1.2 | 1.4 | 76 | 90.4 |
| 2 | 16.7 | — | — | — | — | 11.3 | 67.6 | 5.2 | 311 |
| 3 | 70.2 | 2 | 2.8 | 1.9 | 2.7 | 4.7 | 6.7 | 61.6 | 87 |
| 4 | 70.9 | 2.2 | 3.1 | 1.6 | 2.2 | 2.9 | 4.1 | 64.2 | 90.5 |
| 5 | 70.1 | 1.9 | 2.6 | 0 | 0 | 2.9 | 4.1 | 65.3 | 93 |
| 6 | 90 | 2 | 2.2 | 2.5 | 2.7 | 1.3 | 1.4 | 84.2 | 93.5 |

*MCP = methylcyclopentane
S* = Selectivity.

The activities are given after 15 minutes reaction time. At the exit of the reactor, the percentages by weight of the effluents are determined. The results are shown in Table 1 herein-above in which:

the lights are $C_1$ to $C_5$ paraffins and $C_2$ to $C_4$ olefins.

the isohexanes also contain small quantities of pentene.

methylcyclopentane (MCP) also contains a small quantity of hexanes and benzene comprises traces of toluene, xylene and naphtalene.

1% conversion denotes 1% by weight of hydrocarbons other than n-hexane.

1% selectivity (S) denotes 1% by weight of the products divided by conversion and expressed in %.

It is seen that the treatment by water according to the invention always improves the benzene yield and, in the case of the reground catalyst gives results even higher than those of the initial catalyst.

Of course, the present invention is in no way limited to the examples and methods of realization mentioned herein-above; it is adaptable to numerous modifications accessible to those skilled in the art, according to the applications envisaged and without departing from the spirit of the invention.

We claim:

1. A process for the regeneration of an aromatization catalyst formed of zeolite-L having exchangeable cations of which at least 90% are alkali metal ions and containing platinum which process comprises:
   (a) treating said catalyst with hydrogen;
   (b) subjecting said catalyst obtained from step (a) to calcination;
   (c) subjecting the thereby calcined catalyst to oxychlorination; and
   (d) subsequently subjecting said catalyst to reactivation with hydrogen, wherein after oxychlorination the catalyst is cooled by an air stream containing water at a temperature not exceeding 200° C., the weight proportion of said water with respect to the weight of catalyst being about 10%.

2. A process according to claim 1, wherein the temperature of said air stream containing water is about 60° C.

3. A process according to claim 1, wherein the catalyst is ground prior to calcination.

4. A process according to claim 2, wherein the catalyst is ground prior to calcination.

5. A process according to claim 1 wherein the temperature of the water is atmospheric temperature and the catalyst is ground prior to calcination.

6. A process according to claim 1, wherein said oxychlorination step comprises introducing an air stream containing $CCl_4$, the quantity of said $CCl_4$ being about 1% by weight with respect to the weight of said catalyst.

* * * * *